United States Patent [19]
Szirth et al.

[11] Patent Number: 5,742,375
[45] Date of Patent: Apr. 21, 1998

[54] HEAD MOUNTED LENS SUPPORT

[75] Inventors: Bernard Charles Szirth, Methuen, Mass.; Neil Milton Davis, Eugene, Oreg.

[73] Assignee: Nikon, Inc., Melville, N.Y.

[21] Appl. No.: 653,507

[22] Filed: May 24, 1996

[51] Int. Cl.$^6$ .................................................. A61B 3/04
[52] U.S. Cl. ........................................ 351/229; 351/227
[58] Field of Search ........................... 351/227, 41, 120, 351/158, 228, 229, 230; 359/409, 407, 414, 417

[56] References Cited

U.S. PATENT DOCUMENTS

| | | | |
|---|---|---|---|
| 404,803 | 6/1889 | Smith | 351/227 |
| 610,817 | 9/1898 | May | 351/227 |
| 955,333 | 4/1910 | Hill | 351/227 |
| 1,073,879 | 9/1913 | Tully | 351/227 |
| 1,222,017 | 4/1917 | Moseley | 351/229 |
| 1,266,224 | 5/1918 | Day | 351/229 |
| 1,337,265 | 4/1920 | Poser | 351/229 |
| 1,380,166 | 5/1921 | Wall et al. | 351/227 |
| 1,457,494 | 6/1923 | Bugbee | 351/229 |
| 1,474,788 | 11/1923 | Parsons | 351/227 |
| 1,794,571 | 3/1931 | Wrighton et al. | 351/229 |
| 1,908,053 | 5/1933 | Rigler | 351/227 |
| 2,333,738 | 11/1943 | Peck et al. | 351/229 |
| 4,801,200 | 1/1989 | Hussey | 351/230 |
| 4,850,690 | 7/1989 | Parker et al. | 351/205 |

*Primary Examiner*—Hung X. Dang
*Attorney, Agent, or Firm*—Hughes Hubbard & Reed LLP

[57] ABSTRACT

A head mounted lens support for performing examination and photography of the posterior structures of the eye. The support includes a lateral support to which a pair of adjustable earpieces, and an adjustable nosebridge are attached. Right and left lens positioners are moveably and pivotable attached to the lateral support. The lens positioners each are adjustable by lateral positioners, depth positioners, and angle positioners. The angle positioners swivel from their nominal positions, perpendicular to the lateral support, through an arc of approximately 25 degrees in order to allow full examination of the structures in the posterior chamber of the eye. Right and left lens cradles are attached, respectively, to the ends of the right and left angle positioners. The lens cradles are forms of arc clamps which receive a lens sleeve. The lens sleeve is itself an arc clamp which contains the actual lens.

18 Claims, 2 Drawing Sheets

HEAD MOUNTED LENS SUPPORT

FIELD OF THE INVENTION

This invention generally relates to ophthalmic photography. In particular, this is an apparatus for positioning an aspheric photographic lens at an appropriate distance and angle to the cornea to facilitate observing and photographing the posterior chamber of the eye.

BACKGROUND OF THE INVENTION

The observation of the retina with a slit lamp-biomicroscope and aspheric lens has to this point occurred by holding the aspheric lens in one hand while focusing the slit lamp in the other to facilitate observation of retinal structures. In other cases, the lens would be attached to the slit lamp and held up to the patient's eye.

In prior art methods of photographing the retina, the patient's head typically rested on a support affixed to a table or the floor and the photographer would manually coordinate the camera, slit lamp-biomicroscope and the aspheric lens. The lens must be positioned at an appropriate distance from the cornea at an angle perpendicular to its surface to effectively photograph the retina. In some instances the camera would be attached to a support, but the slit lamp and lens would be positioned by hand.

The problem with this particular method is manifest. There are too many opportunities for movement in the above described process—the patient, the lens, the camera, and the slit lamp all can be shifted independently of each other. The distance and angle between the cornea and the aspheric lens are critical to proper observation and photoreproduction. Small changes in the positioning of any of the elements can render retina photographs useless. The distance between the cornea and lens in most cases should be about 3 millimeters. There should also be a 90° angle between the lens plane and the cornea surface point through which the retina is to be photographed. A small change in the distance and angle between the cornea and the lens can more significantly affect the quality of observation and the photograph, by causing distortion, than a correspondingly small change in the position of the camera or slit lamp.

In the separate field of eye testing, head mounted devices have been employed to position corrective lenses in the vertical and horizontal planes to determine the appropriate corrective lenses required by a particular patient. These positioners do not account for the entirely different requirements of retinal examination addressed by the present invention, however, because they lack the necessary degrees of freedom to position the lens at both the appropriate distance and angle to the cornea.

A principle objective of the present invention is to maintain a stable and fixed distance and angle between an aspheric lens and the patient's cornea.

Another objective of the invention is to make it easier for an examiner or photographer to coordinate the use of the lens, camera, and slit lamp-biomicroscope when observing or photographing a patient's eye.

Another objective of the invention is to make this lens positioner fully adjustable to accommodate a variety of individual patient characteristics, such as interpupilary distance, eyesocket depth, facial bone structure and head size and shape.

A further objective of the invention is to make a lens positioner that is comfortable for the patient.

SUMMARY OF THE INVENTION

The present invention enables the positioning of an aspheric lens at a fixed distance and angle relative to a patient's cornea for the purpose of observing and photographing the retina and other structures of the eye.

The invention comprises a head mounted lens positioner having a lateral frame support, the two ends of which are attached to adjustable earpieces. An adjustable nosebridge is attached to the center of the lateral frame support. Right and left lens support cradles are moveably and pivotaly attached to the lateral frame support. The right lens support is attached at a point between the nosebridge and the right end of the lateral frame support, while the left eye lens support is attached at a point between the nosebridge and left end of the lateral frame support.

Each of the lens support cradles is separately adjustable with respect to the lateral frame support. There are two adjustments associated with each lens support cradle. The first adjustment allows the examiner to move the cradle (and the lens contained therein) towards and away from the patient's eye on an axis perpendicular to the plane of the patient's face. This adjustment is necessary to be able to accommodate the depth of a particular patient's eye socket. The second adjustment allows the examiner to rotate or pivot the lens support cradle in a direction towards the patient's nose or towards the patient's temple. This is an adjustment which is critical for retinal photography since it allows all areas of the posterior chamber to be photographed from different angles.

DESCRIPTION OF THE PREFERRED EMBODIMENT

Figure 1:
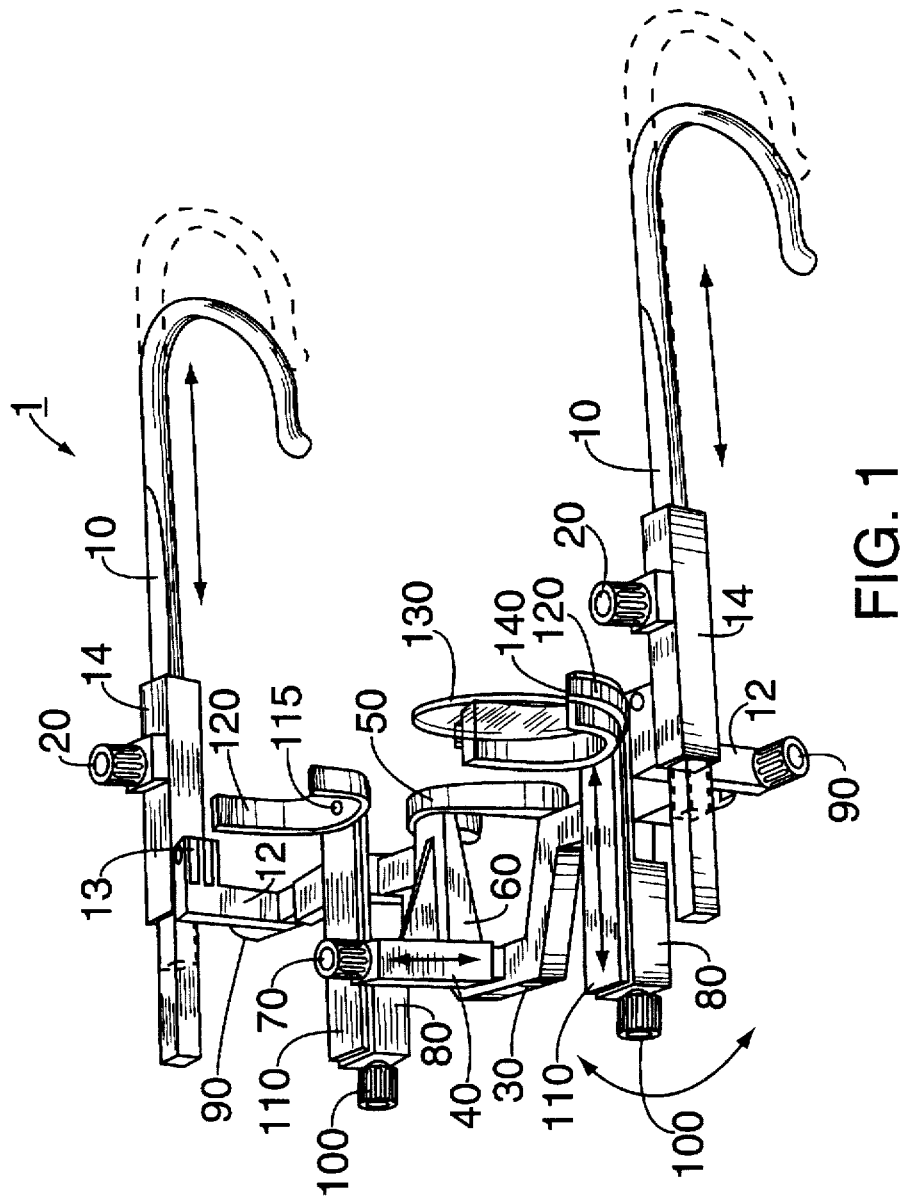
FIG. 1 is a side perspective view of the head mounted lens support of the present invention.

FIG. 1 is a perspective view of an illustrative form of the head mounted lens support of the present invention. As seen in this Figure, the head mount 1 includes a pair of slideably adjustable earpieces 10. In this embodiment, each earpiece 10 is slidably mounted in an earpiece sleeve 14. The earpieces 10 are fixed in position in sleeve 14 by adjustments 20. Adjustments 20 can be spring loaded friction-based mechanisms or simple set screws. In the spring loaded embodiment, earpieces 10 have several detents in the surface facing adjustment 20 which create predefined positions of earpieces 10 when mated with spring loaded mechanism 20. Each earpiece 10 is adjusted to accommodate a particular patient's head by sliding arm 10 through earpiece sleeve 14 to a comfortable but snug fit behind the patient's ears and finally setting arm 10's position with earpiece adjustment 20. The phantom representation of earpieces 10 demonstrates the range of adjustment available for fitting an array of head sizes. Other methods of mounting head mounted support 1 to the patient's head can be employed, such as adjustable straps.

Each sleeve 14 is integrally attached to one end of a lateral frame support 30 through vertical member 12. Sleeves 14 may be pivotably attached to vertical member 12, such as by a hinge mechanism 13. Such an attachment allows folding of the earpieces as one would fold a pair of eyeglasses and also allows flexure of the arms 10 in order to accommodate the varying widths of patient's heads.

An adjustable nose bridge support 40 is attached to the center of lateral frame support 30. Nose rest 50 is attached to support 40 through bridge 60. The combined structure of support 40, bridge 60 and rest 50 is vertically adjustable through a nose bridge adjustment 70. In this embodiment, nose bridge adjustment 70 is a rod and groove mechanism, but other adjustment means may be employed such as a sliding post and sleeve mechanism secured by a set screw. The arrow on support 40 indicates the vertical adjustability of the nose bridge assembly. This vertical adjustment is necessary in order to accommodate the facial structure, particularly the nose of a particular patient.

A pair of lens support members 80 are also attached to lateral frame support 30. Lens support members 80 are laterally adjustable from side to side by a pair of lateral adjustments 90. Lens support members 80 are adjustable toward and away from a patient's eye by a pair of depth adjustments 100. In this embodiment, lateral adjustments 90 and depth adjustments 100 are rod and groove mechanisms, but other adjustment means may be employed such as sliding post and sleeve mechanisms secured by a set screws. The arrow above the right lens support member 80 indicates the depth adjustability of the support member 80.

Lateral adjustments 90 are required to accommodate the varying separation of the eyes (interpupilary distance) found in the patient population. Similarly, depth adjustments 100 are needed because the depth of a patient's eye sockets will vary from patient to patient, and even from eye to eye for a particular patient.

An angle positioner 110 is pivotably attached to each lens support member 80. As shown more clearly in FIG. 2, each angle positioner 110 is pivotally attached to lens support member 80 at pivot point 115. The outboard portion of angle positioner 110 (the portion furthest from the patient's eyes) forms a handle or gripstick by which the examiner may swivel positioner 110 to the proper angle to view the optic disk while the patient is fixating in the primary position. This is particularly useful for Glaucoma detection. The attachment of positioner 110 to support 80 at pivot point 115 is such that positioner 110 is freely pivotable by the examiner, but sufficient tension exists so that positioner 110 will not swivel unless an active force by the examiner is exerted. Once the examiner has placed positioner 110 at a particular desired angle, it will stay in that position regardless of any motion by the patient's head. Alternatively a lock mechanism can be employed in order to secure positioner 110 at a particular angle.

The ability to adjust the angle of aspheric lens 130 with respect to the plane of a patient's eye is a significant advantage of the present invention. The prior art corrective lens devices described in the Background section did not incorporate or even suggest such a pivoting adjustment, because such an adjustment is not required for the use of such devices. The pivoting adjustment of angle positioner 110 enables the examiner to properly position lens 130 with respect to the plane of the patient's eye. Positioner 110 swivels through arc of approximately 25 degrees from its normal position, perpendicular to lateral frame support 30, such that the examiner may photograph the nasal portion of the retina [eye] for Glaucoma detection, and observation of optic disk palor. Similarly, positioner 110 also swivels approximately 25 degrees towards a patient's temple in order to observe that area of the patient's eye chamber.

Figure 3:
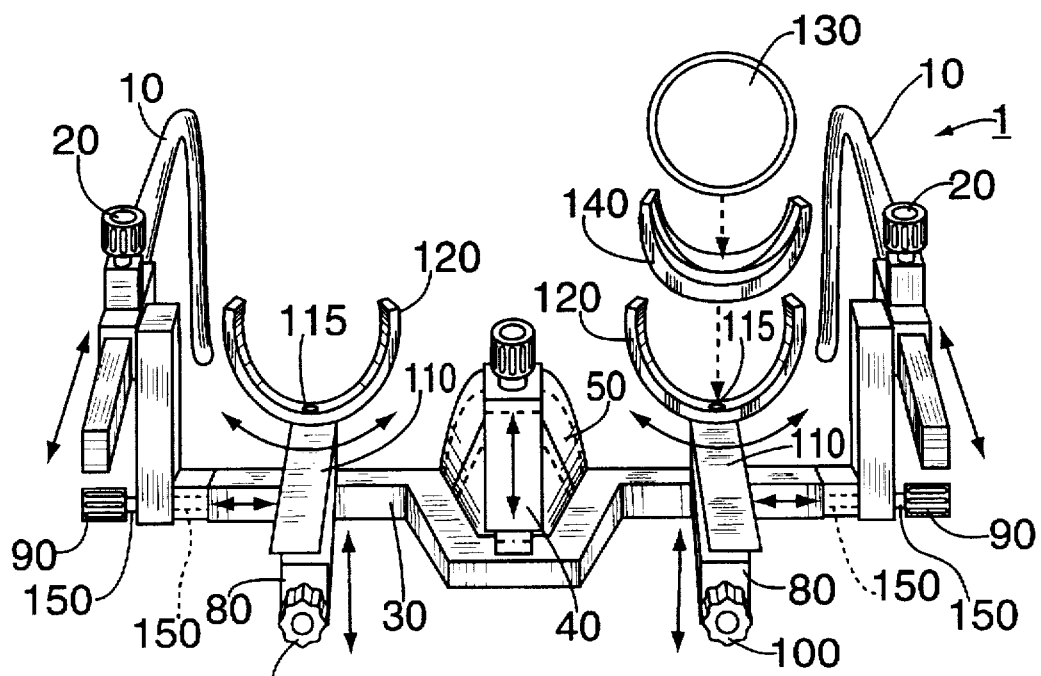
FIG. 3 is a front perspective view of the head mounted lens support.

As seen in FIG. 3, lens sleeve cradle 120 is integrally attached to angle positioner 110 at pivot point 115. An aspheric lens 130 inserted into a lens sleeve 140 by friction fit. Lens sleeve 140 is in turn inserted by friction fit into lens sleeve cradle 120. Other means may also be employed for fastening lens sleeve 140 into the lens sleeve cradle 120, such as by clamping or using a tongue and groove mechanism. Lens sleeve 140 is an important element of the present invention in that it allows the examiner to insert different lenses (e.g. 90 Diopter, 78 Diopter) into support 1 without having to remove support 1 from the patient's head. Additionally, sleeve 140 allows the examiner to handle and change the lens 130 without actually having to touch the surface or edges of lens 130 and potentially mar or scratch the lens (e.g., fingerprints).

Typically, but not necessarily, lens sleeve 140 may consist of an arcuate roughly equal in size to the arcuate of lens sleeve cradle 120. Lens sleeve cradle 120 and lens sleeve 140 are forms of arc clamps. The angle of the arcuate should be slightly larger than 180° to prevent lens 130 from sliding out. Lens sleeve 140 typically, but not necessarily, may comprise an arcuate having a stepped base with two interior circumferences, one sufficiently large to accommodate a press fit lens 130, the other of a smaller circumference to allow the lens 130 to be pressed against it to prevent movement within the lens sleeve 140. Other means may also be employed for securing lens 130 into the lens sleeve 140, such as by using a tongue and groove mechanism.

In the preferred embodiment of the present invention, earpiece sleeve 14, lateral support member 30, bridge 60, lateral adjustment 90, depth adjustment 100, angle positioner 110 and lens cradle holder 120 are made of a structural plastic, but all or a combination of any of these parts can be constructed from other materials, such as light weight metals or composites. To maximize patient comfort and effect proper weight balance, lightweight materials for these components are preferred.

Earpieces 10 typically, but not necessarily, should wrap around the ear to assist with weight balancing of the invention on the patient's face. Earpieces 10 also may be constructed of a flexible material, such as thermo-plastics such as polypropylene or polycarbonate, to increase patient comfort.

In operation, head mounted lens support 1 (FIGS. 1–3), is placed on a patient's face, and arms 10 are adjusted to a comfortable but snug position and secured using adjustment 20. Once positioned on a patient's face, lens sleeve 140 containing lens 130 is inserted into lens sleeve cradle 120 corresponding to the eye to be observed or photographed. Nose bridge 40 is then adjusted vertically by adjustment 70 in order to align the center of lens 130 with centerpoint of the pupil being examined. Once nose bridge 40 is properly adjusted, lateral adjustment 90, depth adjustment 100 and angle positioner 110 are adjusted to achieve the desired distance and angle between lens 130 and the cornea of the patient being examined.

Figure 2:
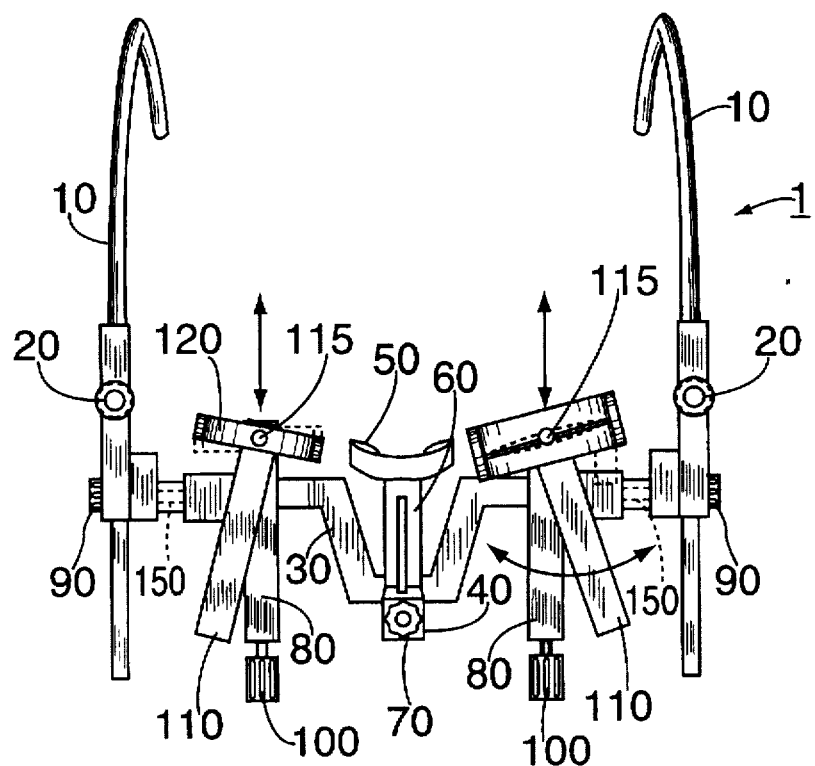
FIG. 2 is a plan view of the head mounted lens support of the present invention.

FIG. 2 shows a top view of an illustrative form of the head mounted lens support 1 of the present invention. In this view, one can more easily see the angular motion of angle positioners 110 about the pivot connection 115 to lens support member 80. The pivot connection 115 to lens support members 80 and angle positioners 110 preferably should contain sufficient tension to maintain the angle of the lens once positioned. The arrows in this Figure indicate the depth and angle adjustability of lens positioner 110 and support 80.

FIG. 3 shows a front perspective view of an illustrative form of the head mounted lens support 1 of the present invention. This view illustrates the full range of adjustment provided by the present invention. The arrows to the outsides of earpieces 10 indicate the direction of eye-ear distance adjustment. The arrows on nose bridge support 40 indicate the direction of its vertical adjustment. The arrows interior to lateral adjustments 90 indicate their direction of adjustment. The arrows to the insides of depth adjustments 100 indicate their direction of adjustment. The arcuate arrows below lens sleeve cradle 120 indicate the radial direction of adjustment of the angle positioners 110.

The dotted shadow of nose piece 50 and nose bridge 40 indicates the range of adjustment 20 for nose bridge 40. It is preferred but not necessary that nose piece 50 be constructed of a soft material such as polypropylene to increase comfort.

Referring to FIG. 3, one can see the threaded rods 150 of lateral adjustments 90 in this embodiment. All of the lens position drive mechanisms employ a very light, easily assembled, inexpensive threaded rod 150 and groove (not shown) mechanical system. Typically but not necessarily, all the drive rods will have the same diameter and the same thread pitch.

The objects of this invention having been demonstrated to have been achieved, the following claims are made with the understanding that they are not exhaustive of the inventive matter contained herein, nor of the numerous modifications and combinations thereof that would be obvious to those skilled in the art without departing from the spirit of this invention.

We claim:

1. A head mounted lens support comprising:
   a lateral support member having a left end and a right end;
   right and left earpieces respectively attached to said right and left ends of said lateral support member;
   a nosebridge attached to said lateral support member;
   right and left lens support members attached to said lateral support member; and
   right and left lens angle positioners pivotally attached, respectively, to said right and left lens support members.

2. The head mounted lens support of claim 1, further comprising:
   right and left lens cradles respectively attached to said right and left lens angle positioners.

3. The head mounted lens support of claim 2, further comprising:
   at least one lens sleeve removeably mounted in one of said lens cradles.

4. The head mounted lens support of claim 3 further comprising:
   a lens removeably mounted in said lens sleeve.

5. The head mounted lens support of claim 4, wherein said lens is an aspheric lens.

6. The head mounted lens support of claim 4, wherein said lens is selected from the group consisting of but not limited to 90 diopter or 78 diopter lenses.

7. The head mounted lens support of claim 3, wherein said lens sleeve is arcurate in shape with an angle of slightly larger than 180 degrees.

8. The head mounted lens support of claim 1, wherein said nose bridge is vertically adjustable with respect to said lateral support member.

9. The head mounted lens support of claim 1, wherein said lateral support member has a main axis, each of said left and right earpieces being separately adjustable in a direction perpendicular to said main axis of said lateral support member.

10. The head mounted lens support of claim 1, wherein said lateral support member has a main axis, each of said left and right lens support members being separately adjustable in a direction perpendicular and parallel to said main axis of said lateral support member.

11. The head mounted lens support of 1, wherein each of said right and left lens angle positioners have a nominal position which is substantially perpendicular to said lateral support member, each of said positioners pivot with respect to said right and left lens support members, respectively, through an angle of approximately twenty five degrees.

12. A head mounted lens support comprising:
   a lateral support member having a centerpoint, a left end and a right end;
   a right earpiece slidably attached to said right end of said lateral support member;
   a left earpiece slidably attached to said left end of said lateral support member;
   a nosebridge moveably attached to said lateral support member at said centerpoint;
   a right lens support member moveably attached to said lateral support member between said centerpoint and said right end of said lateral support member;
   a left lens support member moveably attached to said lateral support member between said centerpoint and said left end of said lateral support member;
   a right lens angle positioner pivotally attached to said right lens support member; and
   a left lens angle positioner pivotally attached to said left lens support member.

13. The head mounted lens positioner of claim 12, wherein said moveable attachment of each of said right and left lens support members to said lateral support member is a rod and groove mechanism to provide lateral movement of said lens support members with respect to said lateral support member.

14. The head mounted lens positioner of claim 12 further comprising right and left depth positioners respectively for said right and left lens support members for enabling movement of said lens support members perpendicular to said lateral movement of said lens support members.

15. The head mounted lens support of claim 12 further comprising right and left lens cradles respectively attached to said right and left lens angle positioners.

16. The head mounted lens positioner of claim 15, wherein said right and left lens support cradles are arc clamps.

17. The head mounted lens positioner of claim 15, further comprising at least one lens sleeve removeable mounted in said right or left lens support cradles.

18. The head mounted lens positioner of claim 15, wherein said right and left angle positioners pivot with respect to said right and left lens support members through and arc of approximately 25 degrees.

* * * * *